United States Patent [19]

Nagel

[11]  4,256,118
[45]  Mar. 17, 1981

[54] APPARATUS FOR THE DETECTION AND RECORDING OF UTERINE ACTIVITY

[75] Inventor: Joachim Nagel, Erlangen, Fed. Rep. of Germany

[73] Assignee: Biotronik Mess-und Therapiegeräte GmbH & Co., Berlin, Fed. Rep. of Germany

[21] Appl. No.: 924,381

[22] Filed: Jul. 13, 1978

[30] Foreign Application Priority Data

Jul. 13, 1977 [DE] Fed. Rep. of Germany ....... 2732160

[51] Int. Cl.³ .............................................. A61B 5/04
[52] U.S. Cl. .................................... 128/733; 128/698
[58] Field of Search ............................... 128/639–644, 128/695–696, 698, 733

[56] References Cited

U.S. PATENT DOCUMENTS

| 3,599,628 | 8/1971  | Abbenante ...................... | 128/698 |
| 3,641,993 | 2/1972  | Gaardner et al. ................ | 128/733 |
| 3,703,168 | 11/1972 | Frink ............................. | 128/639 |
| 3,774,593 | 11/1973 | Hakata et al. .................... | 128/733 |
| 3,811,428 | 5/1974  | Van Horn et al. ................ | 128/639 |
| 3,878,833 | 4/1975  | Arneson et al. .................. | 128/639 |
| 4,149,716 | 4/1979  | Scudder .......................... | 128/733 |

FOREIGN PATENT DOCUMENTS 2134286 7/1970 Fed. Rep. of Germany .......... 128/639

OTHER PUBLICATIONS

DeLuca, C. J. et al., "A Polar Technique for Displaying".
Sureau, "E'tude de l'Activité E'lectrique de l'Uterus au Cours du Travail", Gynécologie et Obstétrique, vol. 55, No. 2, 1956, pp. 153-175.
Fischer, W. M., "Kardioto Kographie", Georg. Thieme Verlag, Stuttgart, Germany (1973).

Primary Examiner—Robert W. Michell
Assistant Examiner—Francis J. Jaworski
Attorney, Agent, or Firm—Spencer & Kaye

[57] ABSTRACT

Apparatus for the detection and recording of uterine activity, particularly for use as a contraction recorder and equipped for the electromyographic detection of the electrical fields in the abdominal region inherent in muscular activity, the apparatus being composed of a system for generating a signal which essentially corresponds to the intensity of the alternating voltage component of the electromyographically derived signal, averaging this signal in time, and emitting the averaged signal as a measure for the intrauterine pressure variations.

22 Claims, 5 Drawing Figures

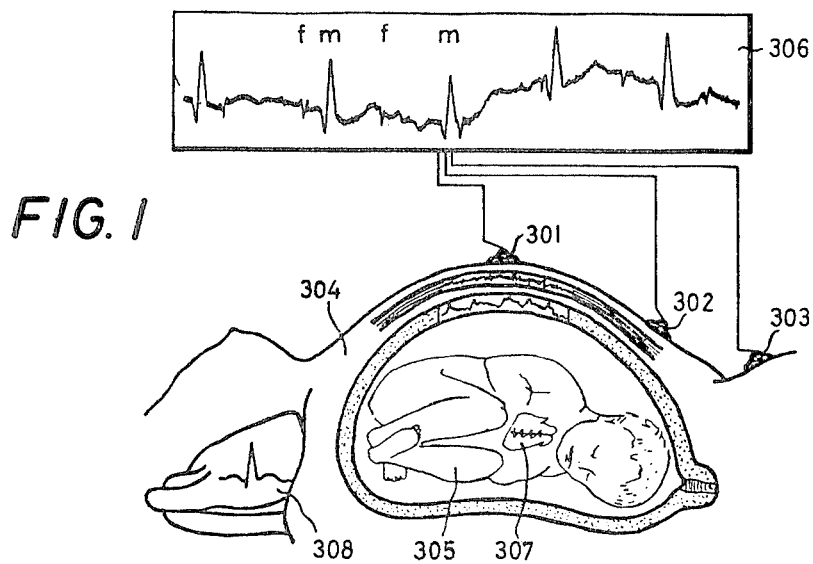
FIG. 1
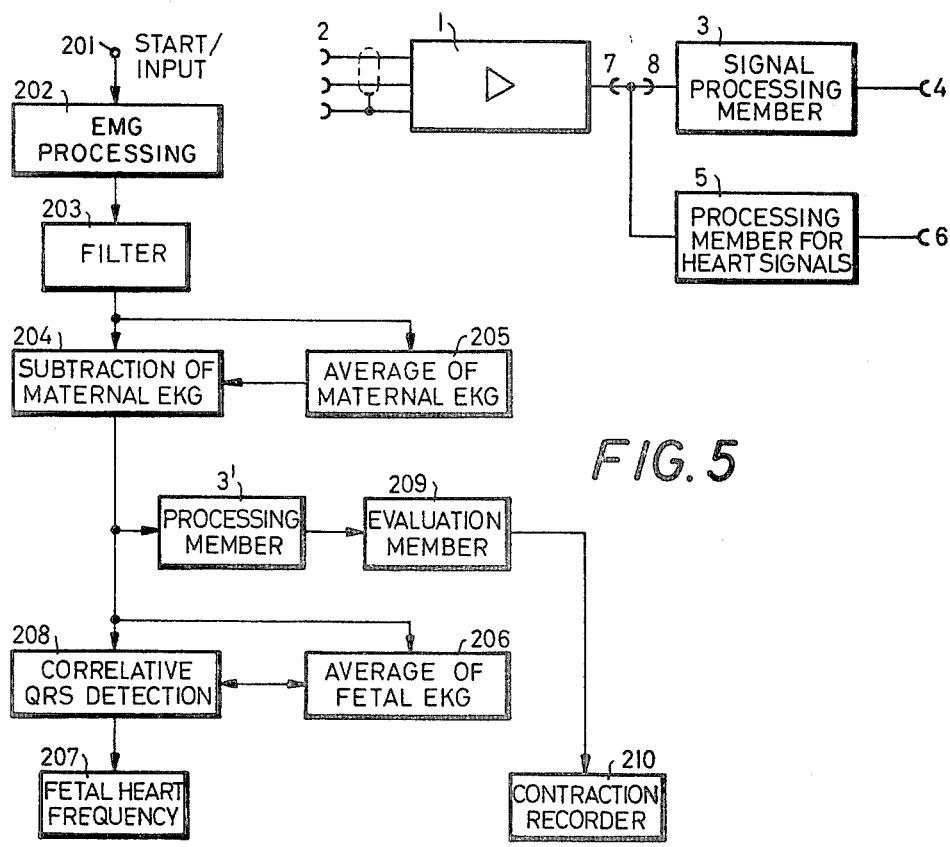
FIG. 2
FIG. 5

APPARATUS FOR THE DETECTION AND RECORDING OF UTERINE ACTIVITY

BACKGROUND OF THE INVENTION

The present invention relates to an apparatus for the detection and recording of uterine activity.

Monitoring and evaluation of uterine activity, which permits the determination of the presence of contractions, is important in perinatal medicine for monitoring the course of pregnancy and evaluating the state of the fetus.

Essentially two methods, an internal and an external method, are known for detecting and recording the intrauterine pressure in the form of a tocogram. Both methods have in common that the uterine pressure is measured at the body by means of pressure sensors.

For internal tocography, the pressure is determined by introducing a fluid-filled, open end catheter into the amnionic cavity or between the amniotic sac and the wall of the uterus. After zero matching has been effected, it is possible with this method to determine the absolute pressure of the uterus.

The internal tocography method is rejected by many physicians due to the difficulty of operation and the risk factor involved. Moreover, most recent tests show that the application of a catheter influences parturition so that this process should not be used for impending premature deliveries where monitoring of the contraction activity would be of particular significance.

External tocography is based on a method disclosed by Rech in 1934. A pressure sensor, which is normally an expansion measuring strip, is fastened to the abdomen of the pregnant patient by means of an elastic strap. Uterine contractions produce changes in the displacement of a sensor pin which acts mechanically on the expansion measuring strip, so that an electrical signal is derived which is a measure for the contraction activity and whose waveform can be evaluated by the treating physician.

External tocography has the drawback that it is an indirect method of pressure recording and is therefore subject to many interfering influences which falsify the measuring result. Such interfering influences include, for example, the changes in pin displacement simply as a result of breathing. This non-invasive method is based on the assumption that the pressure sensed and recorded by the sensor pin constitutes a sufficient approximation of the intrauterine pressure. However, no exact information about the course of the uterine activity can be obtained with this measurement.

Thus both methods have significant drawbacks during routine clinical use so that evaluation of uterus mobility is not used very often and does not produce the results that should be expected from the capability of this method.

SUMMARY OF THE INVENTION

It is therefore an object of the present invention to enable uterine activity to be detected and recorded without encountering the above-mentioned drawbacks and permit an examination which is as comfortable for the patient as possible, and which the treating physician can practice as a matter of routine with a compact instrument and without influencing the parturition process.

Another object of the invention is to permit the measuring results to be evaluated by the physician in a relatively short time and to lead to a safe diagnosis.

These and other objects are achieved according to the invention by providing apparatus which includes means for the electromyographic derivation of a signal representative of the electrical fields inherent in muscular activity in the abdominal region, means for generating a signal corresponding essentially to the intensity of the alternating voltage component of the electromyographically derived signal, means for averaging in time the signal corresponding essentially to the intensity of the alternating voltage component of the electromyographically derived signal, and means for emitting the averaged signal as a measure for the intrauterine pressure.

The invention is based on recognition that changes in intrauterine pressure are produced directly by muscle contractions. The electrical fields connected with these contractions can be electromyographically measured on the surface of the skin. The measured voltage curve is not a direct measure of the intensity of the contractions, but the inventor has discovered that such intensity is represented by an average of the pulse-shaped alternating voltage components of the measured signal. Intensity is here understood to mean a value representative of the amplitude of the alternating voltage component as derived, for example, by rectifying the alternating voltage component or forming a square function, as for a power determination. The emitted signal thus has a curve which is essentially at least similar to the envelope of the electromyographically determined signal.

Thus, there exists a possiblity of measuring the relative uterine pressure purely externally using a measuring technique which does not interfere with the comfort of the patient. Since the signal obtained from electrodes is of an electrical nature, amplification and further processing with subsequent graphic display of the time sequence poses no difficulties. Squaring, in particular, can be effected very easily with circuit means, particularly if an approximate determination is sufficient.

A particularly advantageous feature of a medical examination device according to the present invention is that due to its ease of operation and dependable detection of the signals to be determined, it is particularly suited for routine examinations so that a broad field of application results not only for clinical use.

A further advantage is that although the maternal and the fetal heart signals are contained as interfering signals in the abdominally derived electromyogram, they can be filtered out and evaluated separately.

Furthermore, it is of advantage in the apparatus according to the invention that the information contained in the measurement, and thus available to the physician, is much more extensive than would be the case when pressure sensors are employed. Since skin electrodes are much simpler to attach than mechanical pressure sensors, the procedure involved in the determination of uterine activity is much easier for the physician. The reduction in time spent on examination of a patient also brings about a reduction in treatment costs.

With the apparatus according to the invention, it is possible, by suitable placement of the electrodes, to monitor the activity of the entire uterus as well as the abdominal muscles. From the shape of the detected and displayed contraction curves, conclusions can be drawn as to the excitation and propagation of the contractions. In this way the physician will be able to detect motility problems at an early data as they might occur, for example in connection with incoordination.

Evaluation of the myosignals can advantageously be effected with the use of an appropriate bandpass filter having a pass band in a frequency range of about 150 to 250 Hz. It is of advantage that the signal components from the fetal and from the maternal electrocardiograms, which interfere with the detection of uterine motility, are of a lower amplitude in this frequency range than the myopotentials to be evaluated and therefore have little influence on the result.

A further possibility of reducing the influence of interfering signals during the determination of uterine activity is to select the time constant employed for the average formation, e.g. by lowpass filtering, of the rectified or squared signal to be sufficiently large. When a sufficiently long time constant is provided, it is possible to use even the frequency range of the myographically recorded signal of about 15 to 40 Hz, in which the heart signals have their maximum. The selection of the narrower frequency range to be evaluated and its bandwidth within a total range of about 10 to 300 Hz depends on whether the static or the dynamic components of the muscle contractions are to be given preference and to what extent the influence of the abdominal muscles, e.g tensioning during stage II contractions, is to appear in the result.

The emission of the average signals which constitute a measure for the intrauterine pressure can take place, in an advantageous manner for example, via a connected stylus which gives a logarithmic display so that a broad amplitude range is covered. The amplification factor and the zero line then need not be readjusted so that simple operation is assured.

If the averaged signal is an exponential function, the maxima of the contraction curves become particularly distinct.

Signal processing may be effected in a particularly simple manner by means of analog modules such as operational amplifiers. If the apparatus according to the invention is combined with an apparatus for determining cardiac activity, the signal will advantageously be processed digitally, preferably by means of microprocessors.

The particular advantages of the apparatus according to the invention become evident in the case where abdominally attached electrodes are used to obtain signals from the uterus as well as from fetal or maternal cardiac activity, or in which the received signals are evaluated in a common device. This provides the possibility of obtaining extensive data in a perinatal examination from a signal measurement which gives little discomfort to the patient and which enables the physician to quickly obtain an accurate picture of the state of the fetus and of his patient so that he can immediately take the necessary measures.

If the frequency range to be evaluated is selected, as explained above, together with a correspondingly long time constant for the averaging, so that it also covers the range of the frequencies taken up by the cardiac signals, no further filtering means are required to separate the signals for the determination of the uterine activity from those for the determination of the cardiac activity.

If means are provided to detect interference signals which adversely influence signal evaluation according to a first criterion, to retain their amplitude in a memory, and once the presence of an interference signal in the input signal has been detected, to subtract its amplitude from that of the input signal in the correct phase, this provides the opportunity of eliminating, by ordinary means, signal components such as the maternal QRS complex, which adversely influence the evaluation with respect to the signals relating to uterine activity and to signals relating to cardiac activity. Further evaluation of the cardiac signals can then take place in the manner described in my U.S. Application Ser. No. 896,771, filed on Apr. 14th, 1978. If one or more microprocessors are employed, these can also be used, if programmed appropriately, for the mathematical functions required for the emission of signals relating to the uterine activity.

BRIEF DESCRIPTION OF THE DRAWING

FIG. 1 is a pictorial view of a fetus in a uterus and a plurality of electromyographic electrodes, together with an illustration of the signal generation.

FIG. 2 is a block circuit diagram of a first embodiment of apparatus according to the invention, in which means are simultaneously provided to detect fetal as well as maternal cardiac activity.

FIG. 5 is a block circuit diagram of a second embodiment of the invention, including means for separating the signals to be processed from the interfering maternal heart signals (QRS complexes).

DESCRIPTION OF THE PREFERRED EMBODIMENTS

Figure 3:
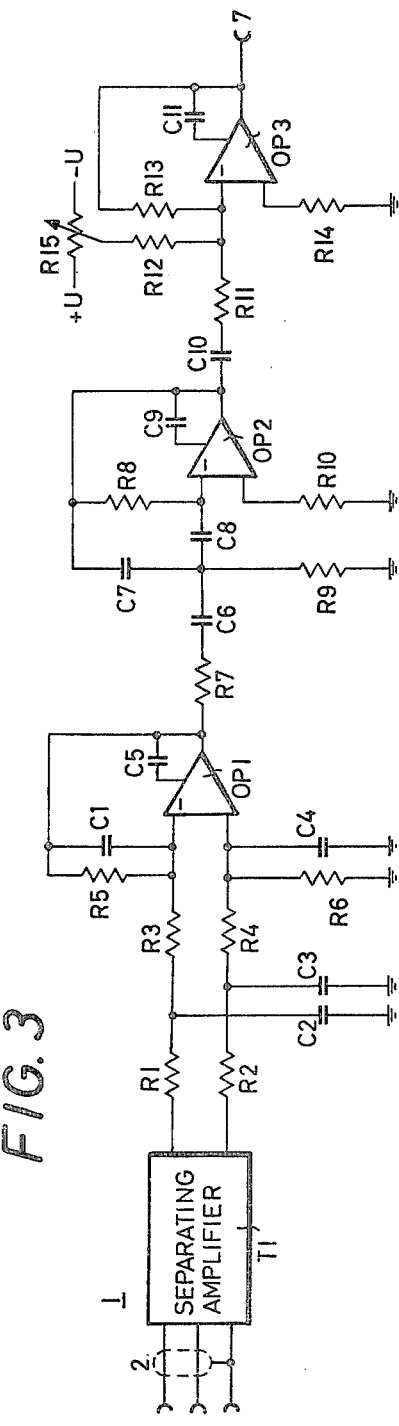
FIG. 3 is a circuit diagram of an embodiment of an amplifier for the electromyographically recorded abdominal signal in the apparatus of FIG. 2.

FIG. 1 illustrates the generation of signals from maternal and fetal muscular activity. Several electrodes 301, 302 and 303 are fastened to the body of a patient 304 whose contraction activity is to be monitored. In one procedure according to the invention the cardiac activity of the fetus 305 is monitored simultaneously. Skin electrodes 301–303 produce electromyographically generated signals having a waveform as shown in graph 306, in which a signal from the heart 307 of the fetus is superposed on a signal from the heart 308 of the mother, and also containing various interference components. Several cycles of the fetal heart signal and of the maternal heart signal are shown in the signal curve 306 and identified by the letters "f" and "m", respectively. The signals representing contraction activity cannot be recognized directly in the recorded signal; they are made evident in the form of curves, i.e. are separated from other information in the total signal, only by the apparatus of the present invention.

A first embodiment of apparatus according to the invention is shown in FIG. 2 and permits determination and recording of uterus activity by detection and indication of muscle contractions in the abdominal region. The input of an amplifier 1, one embodiment of which is shown in detail in FIG. 3, is connected via its inputs 2 to the electrodes 301–303, which are not shown in FIG. 2.

Figure 4:
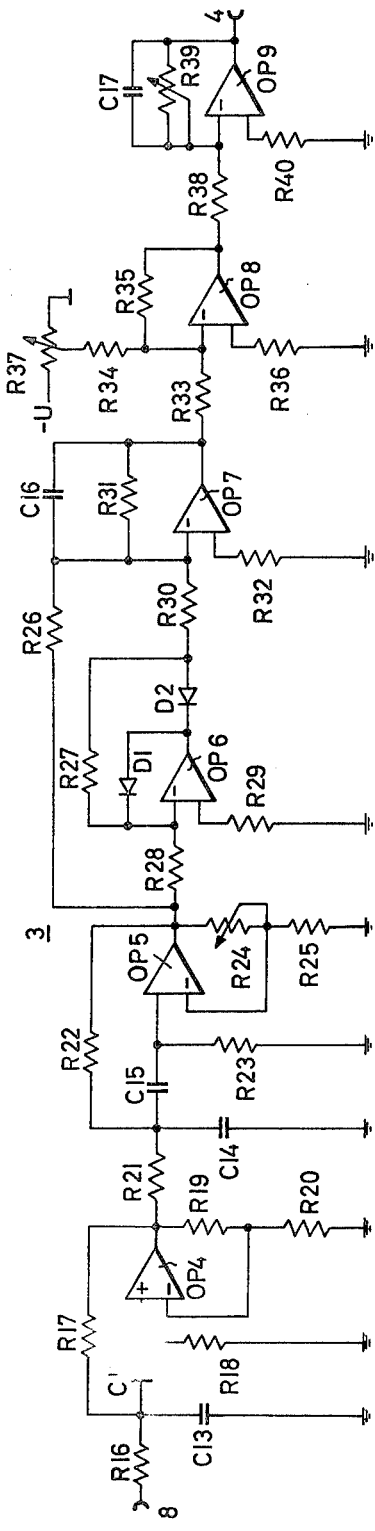
FIG. 4 is a circuit diagram of an embodiment of the processing portion for the electromyogram in the apparatus of FIG. 2.

The signal from the output 7 of amplifier 1 is fed to an input 8 of a processing member 3 in which the signals representing the uterine activity are processed to produce a signal at output 4 which is representative of the uterine motility, or movements. A recording device (not shown) is connected to the output 4 to record a curve for the intensity of the contraction activity in dependence on time so that the physician can draw conclusions as to the contraction activity from the resulting characteristic curve shapes, perhaps by comparison with a list of reference curve shapes. Details of the circuitry of one embodiment of processing member 3 are shown in FIG. 4.

The illustrated embodiment of the apparatus according to the invention is simultaneously capable of deriving information about the cardiac activity from the signal curve recorded with but a single electrode arrangement. For this purpose, the signal at the output 7 of amplifier 1 is branched off to a processing member 5 for the heart signals. The manner of dividing the signals between members 3 and 5 will be explained further below. At the output 6 of processing member 5, there appears a fetal electrocardiogram, or a signal which is a measure of the heart frequency, which can be recorded, for example, in the form of a time-dependent curve. The display of the fetal heart signals can be combined with that of the signals of the uterine activity in a cardiotocogram, which may be displayed in a single graphic display device.

FIG. 3 shows the complete circuit diagram for an embodiment of the amplifier 1 for the abdominal signal in the apparatus of FIG. 2. The signals from the abdominal electrodes 301–303 travel via inputs 2 to a separating amplifier T1 which serves to separate the potential of the patient from that of the measuring instrument. Separating amplifier T1 can either be a transformer coupled or optically coupled amplifier, that is designed to guarantee patient safety current limits proposed by the U.L. and AAMI, e.g. Analog Devices Model 276J isolation amplifier.

The outputs of the separating amplifier T1 are connected to the inputs of a differential which includes an operational amplifier OP1 equipped with resistors R1 to R6 and capacitors C1 to C5. Resistors R1 and R3 and capacitor C2 form an input lowpass filter, as do resistors R2 and R4 and capacitor C3, while the resistor-capacitor combinations C1/R5 and C4/R6 as well as capacitor C5 act to reduce the amplifier gain with respect to higher frequency signal components.

The subsequent stage containing operational amplifier OP2, resistors R7 to R10 and capacitors C6 to C9 is connected in a conventional manner as a frequency selective filter. In the illustrated embodiment the values of resistors R7 to R10 and those of capacitors C6 to C9 are selected so that the circuit preferably trims, or attenuates the low frequency components of the abdominal signal.

The last stage containing operational amplifier OP3, resistors R11 to R15, and capacitors C10 and C11 operates as a purely alternating voltage coupled amplifier circuit. The amplification factor of this amplifier circuit is determined by the ratio of the resistance values of resistors R11 and R13. Zero matching, or setting of the output signal can be effected via resistor R12 by means of a variable resistance R15. The total amplifier circuit for the abdominal signal produces a first trimming, or suppression, of the frequency components which are undesirable for the subsequent signal processing.

FIG. 4 shows an embodiment of the circuit of the processing member 3 for the electromyogram in the apparatus of FIG. 2. The first two stages including the operational amplifiers OP4 and OP5, resistors R16 to R25 and capacitors C12 to C15 act as a bandpass filter for the signal appearing at the input of processing member 3. The bandpass filter produces a pass band between the frequency limits $f_{lower}=150$ Hz and $f_{upper}=250$ Hz, since in this frequency range the power of the uterine action potentials exceeds that of the interference components. The connection of operational amplifiers OP4 and OP5 with resistors R16 to R26 and capacitors C12 and C15 corresponds in function to that of operational amplifier OP2 in FIG. 3. The values of the individual components are given in a parts list set out below. They are selected according to the rules applicable for such active filter circuits. The output level from the bandpass filter can be set by means of variable resistance R24.

The operational amplifiers OP6 and OP7, resistors R26 to R32, capacitor C16 and diodes D1 and D2 are connected to form an integrating full-wave rectifier, the output signal from which constitutes a good approximation of the effective (RMS) value of the uterine action potential, the structure of the circuit employed being simple compared to a squaring circuit and producing dependable operation.

The first stage, including operational amplifier OP6 and its associated passive components, forms a half-wave rectifier, while the second stage, including operational amplifier OP7 and its associated passive components, acts as an integrating adder and adds to the input signal from the preceding stage appearing at its input via resistor R26 the rectified negative polarity half-waves from the preceding stage applied via resistor R30.

The capacitor C16 and the resistor R31 provide the circuit with the necessary lowpass characteristic to enable it to effect an average formation. The value of the time constant which they provide amounts to several seconds (for example, in excess of five seconds) and determines, on the one hand, the response to the time sequence of the uterine muscular activity, in that a small time constant results in high time resolution, while a higher selected time constant causes individual contractions to stand out more clearly, and, on the other hand, the evaluatable frequency range. With a longer selected time constant, i.e. longer than about 10 seconds, it becomes possible to also utilize those frequency ranges for the determination of the uterine activity on which the cardiac signals are superposed. This provides a structurally particularly simple embodiment in which no separate filtering means for eliminating, in particular, the maternal heart signal, are required.

The subsequent stage including the operational amplifier OP8 and resistors R33 to R37 can be used to set the zero line of the output signal by adjustment of variable resistor R37. Otherwise this stage serves as an amplifier with an amplification factor corresponding to the ratio of the resistance values of resistors R35 and R33.

The last stage, which includes the operational amplifier OP9, resistors R38–R40 and capacitor C17, forms a final amplifier for the output signal, its output level being adjustable by adjustment of variable resistor R39. Capacitor C17 produces an additional lowering of the upper frequency range so that a recording device connected to the output of the operational amplifier OP9 is protected against surge-like deflections.

In the above-described embodiment of the apparatus according to the invention, use is made in an advantageous manner of the fact that a limited frequency band of about 150 to 250 Hz contains significant signals which are characteristic of uterine motility. This makes it possible, on the one hand, to provide a simple, dependably operating device for the detection of these signals which separates the useful signals by uncomplicated means, such as frequency filters, from the interfering signals. Simultaneously a separation may be effected of the fetal and maternal heart signals which are to be evaluated separately as shown schematically in FIG. 2 since the frequency range which is characteristic for cardiac activity lies approximately between 15 and 40 Hz. The total signal S(t) picked up by the electrodes 301-303 of FIG. 1 has the following composition:

$$S(t) = D(t) \cdot [E_f(t) + E_m(t) + EMG + N(t)].$$

where
 D(t) is a multiplicative distortion factor,
 $E_f(t)$ is the fetal heart signal,
 $E_m(t)$ is the maternal heart signal,
 EMG is the component of the electromyogram which is characteristic for the uterine activity and
 N(t) is an additive interference component.

The influence of D(t) is very small and can be neglected without adversely affecting the measuring result.

If the time constant for the time averaging is made sufficiently long, frequency separation of the signal components characteristic for uterine and cardiac activity need not be made since for time constants of more than about 10 seconds, the heart signals no longer have an interfering effect in the evaluation of uterine activity. Thus the bandpass filter shown in the upper portion of FIG. 4 need not be used in this case while a corresponding filter for a frequency range from about 15 to 40 Hz which had originally been provided in processing member 5 can be associated with amplifier 1 so that in the entire arrangement only one bandpass filter is required.

After filtering out the EMG component, the remaining signal is preferably processed in a system as described in my U.S. Application Ser. No. 896,771, filed on Apr. 14th, 1978, now U.S. Pat. No. 4,211,237, and shown schematically in FIG. 5, which depicts a basic embodiment of the present invention in which the elimination of repeated interfering signal components and the detection of the fetal heart frequency is effected in the same manner as illustrated in the above-mentioned patent application.

Point 201 represents either the input of an electrical circuit or the starting point of a computer program. Stage 202 includes all steps connected with the pick up of the electromyographically derived signal.

The myographically derived signal picked up is freed of interfering signal components in a filtering stage 203, and in the subsequent stage 204 the maternal heart signal is removed from the filtered input signal by subtraction. That which is substracted in stage 204 is a signal curve which corresponds to the average maternal EKG, this curve being obtained by detecting the maternal EKG and employing average formation to effect continuous correction. The average maternal EKG signal is formed and retained in stage 205. During subtraction the amplitude of the signal to be subtracted is adapted to the amplitude of the input signal.

The signal thus freed of interfering components serves as the input signal for a signal processing member 3' in which the signals relating to uterine activity are processed as described in connection with processing member 3 of FIGS. 2 and 4. However, in contradistinction to the processing member 3 shown in FIG. 4, the processing member 3' has no bandpass filter component group since filtering is effected in common, for all parts of the system, by filter 203. In an evaluation member 209 the amplitude values emitted from member 3' can be logarithmically or exponentially distorted and they are then graphically displayed in dependence on time in a contraction recorder 210.

In a stage 206, subsequent to the other signal path the fetal EKG signal is actually determined and its average is stored. Initially the presence of a fetal heart signal is detected by means of a maximum criterion and during the later course of the procedure a second criterion used to determine the presence of a fetal heart signal is the degree of coincidence between the curve of the input signal and the stored average, i.e. the sample signal, which itself is continuously adapted to the actual signal shape. The average of the fetal EKG, or its QRS complex, is formed in stage 208 while the fetal heart frequency is calculated from the time intervals between the fetal heart signals and is recorded in stage 207.

The embodiment of the apparatus according to the invention shown in FIGS. 3 and 4 is preferably formed of analog components. Such an apparatus can be produced with particular advantage if it is to be used by itself. In digital design, in which, for use in connection with other detection devices for patient data, available data processing devices such as microprocessors can be used as well, programs or partial programs as they are included, for example, in program collections, or libraries, available for appropriate data processing devices or microprocessors, e.g. LSI 11 or 8080, can be employed for the necessary mathematical calculations, which include average formation, power determination, RMS-detection, logarithm formation, exponential rises, etc.

In a practical embodiment of the circuit shown in FIG. 3, the components can have the following values:

| | |
|---|---|
| R1, R2 | 680 |
| R3, R4 | 150 |
| R5, R6, R15 | 4,7K |
| R7, R10 | 1k |
| R8 | 333,3k |
| R9 | 253k |
| R11, R14 | 2,7K |
| R12 | 56k |
| R13 | 27k |
| C1, C4 | 0,1µ |
| C2, C3 | 68n |
| C5, C9, C11 | 390p |
| C6, C7, C8 | 2,2µ |
| C10 | 100µ |
| Operational amplifiers OP1, OP2 and OP3 can be of the type | AD 504 L |

Similarly, in a practical embodiment of the circuit shown in FIG. 4, the components can have the following values:

| | |
|---|---|
| R16, R17, R18, R20, R21, R22, | 10k |
| R23, R25, R27, R28, R30, R31 | 10k |
| R33, R34, R35 | 10k |
| R19 | 22k |
| R24 | 100k |
| R26, R38 | 20k |
| R29 | 5k |
| R32 | 6,8k |
| R36 | 5,6k |
| R39 | 250k |
| R40 | 18k |
| R47 | 1k |
| C12, C13 | 0,15µ |
| C14, C15 | 0,10µ |

| -continued | |
|---|---|
| C16 | 150μ |
| C17 | 2,2μ |
| Operational amplifiers | |
| OP4, OP5, OP6, OP7, OP8 and OP9 can be of the type | μA 741 |
| Diodes D1 and D2 can be of the type | IN 4148 |

It will be understood that the above description of the present invention is susceptible to various modifications, changes and adaptations, and the same are intended to be comprehended within the meaning and range of equivalents of the appended claims.

What is claimed is:

1. Apparatus for detecting and recording the uterine pressure of a subject, comprising:
   detection means for effecting electromyographic detection of electrical fields inherent in muscular activity in the abdominal area of the subject and for producing a corresponding signal;
   generating means connected to the output of said detection means for generating a signal which corresponds to the intensity of the alternating voltage component of the electromyographically detected signal at the output of said detection means;
   means connected to said signal generating means for averaging in time the signal which corresponds essentially to the intensity of the alternating voltage component of the electromyographically detected signal; and
   emitting means connected to said averaging means for emitting a representation of the time averaged signal as a measure of the intrauterine pressure.

2. An arrangement as defined in claim 1 wherein said generating means acts to emit a signal which is a measure of the electrical power of the alternating voltage component of the electromyographically detected signal.

3. An arrangement as defined in claim 1 wherein said generating means comprises means for rectifying the alternating voltage component of the electromyographically detected signal.

4. An arrangement as defined in claim 3 wherein said generating means effects a quadratic averaging of such component.

5. An arrangement as defined in claim 1 wherein said generating means acts to emit a signal which corresponds to the effective (RMS) value of the alternating voltage component of the electromyographically detected signal.

6. An arrangement as defined in claim 1 wherein said means for averaging in time comprises a lowpass filter.

7. An arrangement as defined in claim 6 wherein the time constant of said lowpass filter is longer than 5 seconds.

8. An arrangement as defined in claim 7 wherein the time constant of said lowpass filter is longer than 10 seconds.

9. An arrangement as defined in claim 1 further comprising filter means for causing the signal from said generating means to be constituted by a given frequency range of the alternating voltage component of the electromyographically deteted signal.

10. An arrangement as defined in claim 9 wherein the given frequency range lies between 150 and 250 Hz.

11. An arrangement as defined in claim 1 wherein said emitting means are arranged to display a logarithmic function of the averaged signal.

12. An arrangement as defined in claim 1 wherein said emitting means is arranged to display an exponential function of the averaged signal.

13. An arrangement as defined in claim 1 wherein said generating means is provided for the detection and recording of uterine pressure and of heart signals.

14. An arrangement as defined in claim 1 wherein said detection means is provided for the detection and recording of uterine pressure and of heart signals.

15. An arrangement as defined in claim 14 wherein myographically detected signals from said detection means are limited to a frequency range from 15 to 40 Hz for purposes of evaluation.

16. An arrangement as defined in claim 14 further comprising means connected for detecting, according to a first criterion, repeated interference signals which adversely influence signal evaluation by storing a representation of a selected component of the detected signal in a memory and, once the occurrence of interference signals in the detected signal has been determined, by subtracting such interference signals from the detected signal in the correct phase.

17. An arrangement as defined in claim 16 for detecting fetal heart signals, wherein the repeated interference signal is the maternal QRS complex.

18. An arrangement as defined in claim 14 comprising means for the detection of the QRS complexes of fetal heart signals in a signal portion separated from the detected signal including a memory for retaining a representation of the amplitude curve of a fetal QRS complex which has been recognized according to a first criterion, and means using said QRS complex as a sample for the identification of subsequent QRS complexes according to a second criterion based on the degree of coincidence of the detected signal with the amplitude curve representation retained in said memory.

19. An arrangement as defined in claim 18 further comprising means for continuously adapting the amplitude curve of the fetal QRS complex, which has been retained in said memory, to the actual shape of the fetal QRS complex.

20. Apparatus for detecting and measuring the uterine pressure of a subject, comprising:
   electromyographic detection means for detecting electrical inherent in muscular activity in the abdominal area of said subject and for producing detection voltages corresponding thereto, said detection voltages having alternating voltage components,
   a bandpass filter coupled to said detection means for transmitting the alternating voltage components of said detection voltages in the frequency range 150 to 250 Hz, said frequency range being that in which interference components in said detection voltage are less than components corresponding to said uterine pressure,
   an integrating full-wave rectifier coupled to the output of said bandpass filter for producing a voltage substantially corresponding to the effective (RMS) value of the voltage at the output of said electromyograpic detection means, and
   indicating means coupled to the output of said integrating full-wave rectifier for measurement of said uterine pressure.

21. Apparatus as defined by claim 20 wherein said integrating full-wave rectifier comprises:
   a half-wave rectifier having an input coupled to the output of said bandpass filter, and an integrating adder having an input coupled to the output of said bandpass filter and to the output of said half-wave rectifier, said integrating adder including an averaging circuit having a time constant which produces at the output of said integrating adder an average of the alternating voltage components at the output of said bandpass filter.

22. Apparatus as defined by claim 21 wherein the time constant of said integrating adder is longer than five seconds.